US012066421B2

United States Patent
Nagashima et al.

(10) Patent No.: US 12,066,421 B2
(45) Date of Patent: Aug. 20, 2024

(54) METHOD FOR DETERMINING REFERENCE VALUE OF WINE FOR FEASIBILITY OF FILLING ALUMINUM CAN, METHOD FOR CHECKING FEASIBILITY OF FILLING ALUMINUM CAN WITH WINE, AND METHOD FOR PRODUCING ALUMINUM-CANNED WINE

(71) Applicant: DAIWA CAN COMPANY, Tokyo (JP)

(72) Inventors: Akira Nagashima, Tokyo (JP); Koichiro Nakamura, Sagamihara (JP); Sin Ou, Tokyo (JP)

(73) Assignee: Daiwa Can Company, Tokyo (JP)

( * ) Notice: Subject to any disclaimer, the term of this patent is extended or adjusted under 35 U.S.C. 154(b) by 0 days.

(21) Appl. No.: 18/470,891

(22) Filed: Sep. 20, 2023

(65) Prior Publication Data

US 2024/0011963 A1  Jan. 11, 2024

Related U.S. Application Data

(63) Continuation of application No. PCT/JP2021/013901, filed on Mar. 31, 2021.

(51) Int. Cl.
*G01N 33/14* (2006.01)
*B32B 7/12* (2006.01)
(Continued)

(52) U.S. Cl.
CPC .............. *G01N 33/146* (2013.01); *B32B 7/12* (2013.01); *B32B 15/09* (2013.01); *B32B 15/20* (2013.01);
(Continued)

(58) Field of Classification Search
CPC ........ G01N 33/14; G01N 33/146; B32B 7/12; B32B 15/09; B32B 15/20; B32B 27/36;
(Continued)

(56) References Cited

U.S. PATENT DOCUMENTS 4,490,042 A * 12/1984 Wyatt .................... G01N 21/51
356/343
5,200,909 A * 4/1993 Juergens ................ G01N 33/14
436/24
(Continued)

FOREIGN PATENT DOCUMENTS

JP  2006-062688 A  3/2006
JP  2009-113217 A  5/2009
(Continued)

OTHER PUBLICATIONS

International Search Report dated Jun. 22, 2021 received in PCT/JP2021/013901.
(Continued)

*Primary Examiner* — Natalie Huls
(74) *Attorney, Agent, or Firm* — Scully, Scott, Murphy & Presser, P.C.

(57) ABSTRACT

A method for determining a reference value of a wine for feasibility of filling an aluminum can, the method comprising: acquiring a pH, an alcohol concentration, and a free sulfite concentration for multiple kinds of wines; calculating a molecular $SO_2$ concentration of each of the multiple kinds of wines from acquired values of the pH, the alcohol concentration, and the free sulfite concentration; enclosing the multiple kinds of wines into aluminum cans of an identical type, respectively, thereby obtaining multiple kinds of canned wines; putting the multiple kinds of canned wines in storage and evaluating quality of the canned wines after the storage; and determining an upper limit value of the molecular $SO_2$ concentration based on an evaluation result obtained from the evaluating.

12 Claims, 3 Drawing Sheets

(51) Int. Cl.
    *B32B 15/09*     (2006.01)
    *B32B 15/20*     (2006.01)
    *B32B 27/36*     (2006.01)
    *B65D 23/02*     (2006.01)
    *B67C 3/02*     (2006.01)

(52) U.S. Cl.
    CPC .............. *B32B 27/36* (2013.01); *B65D 23/02* (2013.01); *B67C 3/02* (2013.01); *B32B 2255/06* (2013.01); *B32B 2255/26* (2013.01); *B32B 2255/28* (2013.01); *B32B 2270/00* (2013.01); *B32B 2439/66* (2013.01)

(58) Field of Classification Search
    CPC ............ B32B 2255/06; B32B 2255/26; B32B 2255/28; B32B 2270/00; B32B 439/06; B65D 23/02; B65D 7/04
    See application file for complete search history.

(56) References Cited

U.S. PATENT DOCUMENTS

| | | | | |
|---|---|---|---|---|
| 10,996,207 | B1* | 5/2021 | Taheri | B65D 85/72 |
| 2003/0059561 | A1* | 3/2003 | Ueda | B65D 23/02 |
| | | | | 428/35.7 |
| 2013/0203171 | A1 | 8/2013 | Sportsman | |
| 2015/0079253 | A1* | 3/2015 | Stokes | C12H 1/063 |
| | | | | 426/326 |
| 2015/0293067 | A1* | 10/2015 | Greene | G01N 33/0042 |
| | | | | 356/72 |
| 2020/0363382 | A1* | 11/2020 | Schmitt | G01N 33/14 |
| 2021/0031981 | A1* | 2/2021 | Kitou | B32B 1/00 |
| 2021/0372932 | A1* | 12/2021 | Gilliam | G01N 21/65 |
| 2022/0195354 | A1* | 6/2022 | Sommer | A23L 2/42 |
| 2023/0236121 | A1* | 7/2023 | Slone | G01N 33/0047 |
| | | | | 250/338.1 |
| 2024/0010388 | A1* | 1/2024 | Nagashima | B65D 1/16 |

FOREIGN PATENT DOCUMENTS

| | | |
|---|---|---|
| JP | 2011-016570 A | 1/2011 |
| WO | 2003/029089 A1 | 4/2003 |
| WO | WO-2013091029 A1 * | 6/2013 .......... B01D 61/142 |
| WO | 2019/151189 A1 | 8/2019 |

OTHER PUBLICATIONS

Translation of the International Preliminary Report on Patentability dated Oct. 3, 2023 and Written Opinion of the International Searching Authority dated Jun. 22, 2021 received in PCT/JP2021/013901.

* cited by examiner

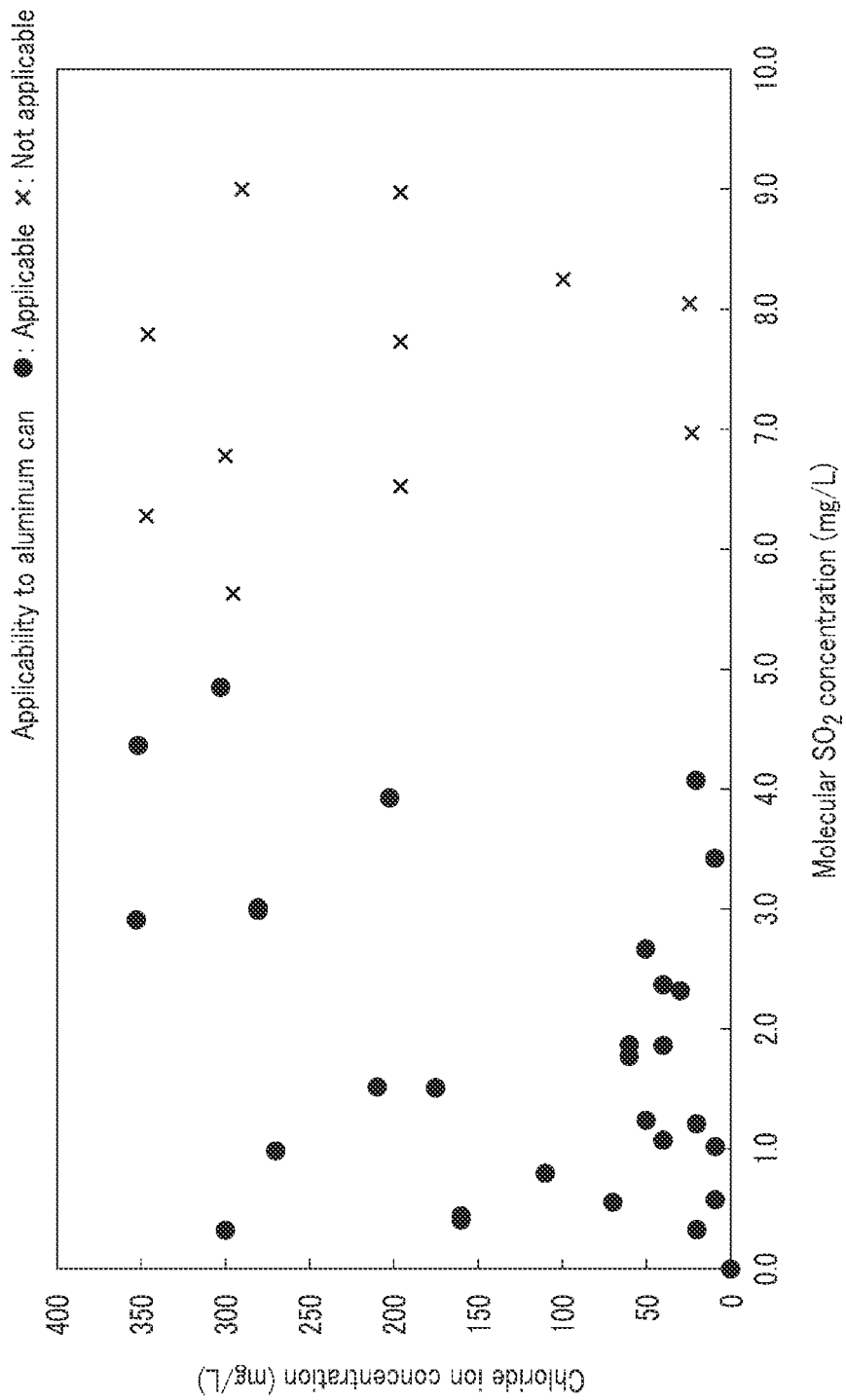
F I G. 4

METHOD FOR DETERMINING REFERENCE VALUE OF WINE FOR FEASIBILITY OF FILLING ALUMINUM CAN, METHOD FOR CHECKING FEASIBILITY OF FILLING ALUMINUM CAN WITH WINE, AND METHOD FOR PRODUCING ALUMINUM-CANNED WINE

CROSS-REFERENCE TO RELATED APPLICATIONS

This application is a Continuation Application of PCT Application No. PCT/JP2021/013901 filed Mar. 31, 2021, the entire contents of which are incorporated herein by reference.

FIELD

The present invention relates to a method for determining a reference value of a wine for feasibility of filling an aluminum can, a method for checking feasibility of filling an aluminum can with a wine, and a method for producing an aluminum-canned wine.

BACKGROUND

Wines generally contain a proper amount of sulfite as an essential additive for the suppression of wild yeast during juice fermentation and for the control of aging. Filling an aluminum can with such a wine may cause problems wherein the aluminum can is easily corroded due to the corrosiveness of sulfite added to the wine and wherein a redox reaction occurs between the sulfite and aluminum to generate hydrogen sulfide, which degrades the wine flavor.

Sulfite added to wine is partly present as "combined sulfite", bonded to saccharide, aldehyde, anthocyanin, etc., and the remaining sulfite is present as "free sulfite". A major part of free sulfite takes the form of $HSO_3^-$ (bisulfite ion), while the other part takes the form of $SO_2$ (molecular $SO_2$). The abundance ratio between the bisulfite ions and the molecular $SO_2$ varies according to pH.

For example, Patent Literature 1 is directed to a method for packaging a wine in an aluminum can, and discloses production of a wine containing less than 35 ppm free sulfite, less than 300 ppm chloride, and less than 800 ppm sulfate, and application of corrosion resistant coating onto the inner surface of an aluminum can.

CITATION LIST

Patent Literature

Patent Document 1: International Publication No. 03/029089

SUMMARY

Technical Problem

Presently, for the commercialization of aluminum-canned wines, whether or not corrosion of aluminum cans would occur is checked for each combination of a wine and an aluminum can by filling a subject aluminum can with a subject wine and having it undergo a storage test (a test involving a storage period of, for example, one month to one year). This makes the commercialization of aluminum-canned wines time-consuming. The present inventors have focused on this problem and attempted to solve the problem. The objects of the present invention thus include providing a novel method for reducing a time required for the commercialization of aluminum-canned wines.

Solution to Problem

The present inventors have discovered that there is a close correlation between the concentration of molecular $SO_2$ in wines and corrosion of aluminum cans and have accomplished the present invention.

More specifically, the present inventors have accomplished the present invention with the new finding that if a reference value of a wine (i.e., an upper limit value of the molecular $SO_2$ concentration of a wine) feasible for filling is determined for each aluminum can type in advance, it is possible to check whether or not filling a subject aluminum can with a subject wine is feasible based on this reference value.

Here, according to a first aspect of the present invention, there is provided a method for determining a reference value of a wine for feasibility of filling an aluminum can, the method comprising:

acquiring a pH, an alcohol concentration, and a free sulfite concentration for multiple kinds of wines;

calculating a molecular $SO_2$ concentration of each of the multiple kinds of wines from acquired values of the pH, the alcohol concentration, and the free sulfite concentration;

enclosing the multiple kinds of wines into aluminum cans of an identical type, respectively, thereby obtaining multiple kinds of canned wines;

putting the multiple kinds of canned wines in storage and evaluating quality of the canned wines after the storage; and determining an upper limit value of the molecular $SO_2$ concentration based on an evaluation result obtained from the evaluating.

According to a second aspect of the present invention, there is provided a method for checking feasibility of filling an aluminum can with a wine, the method comprising:

acquiring a pH, an alcohol concentration, and a free sulfite concentration for a subject wine intended to be enclosed in an aluminum can used in the method according to the first aspect;

calculating a molecular $SO_2$ concentration of the subject wine from acquired values of the pH, the alcohol concentration, and the free sulfite concentration; and excluding the subject wine from wines that are feasible for filling the aluminum can used in the method according to the first aspect if the calculated molecular $SO_2$ concentration exceeds the upper limit value of the molecular $SO_2$ concentration determined by the method according to the first aspect.

According to a third aspect of the present invention, there is provided a method for producing an aluminum-canned wine, the method comprising:

enclosing a subject wine determined to have a filling feasibility by the method according to the second aspect into an aluminum can of an identical type to the aluminum can used in the method according to the first aspect.

Advantageous Effects of Invention

With the method of the present invention, a time required for the commercialization of aluminum-canned wines can be reduced while ensuring the corrosion resistant characteristics of aluminum cans.

BRIEF DESCRIPTION OF THE DRAWINGS

FIG. 4 is a scatter diagram expressing influences of the molecular $SO_2$ concentration and the chloride ion concentration of a wine on the applicability to the aluminum can.

DETAILED DESCRIPTION

Figure 1:
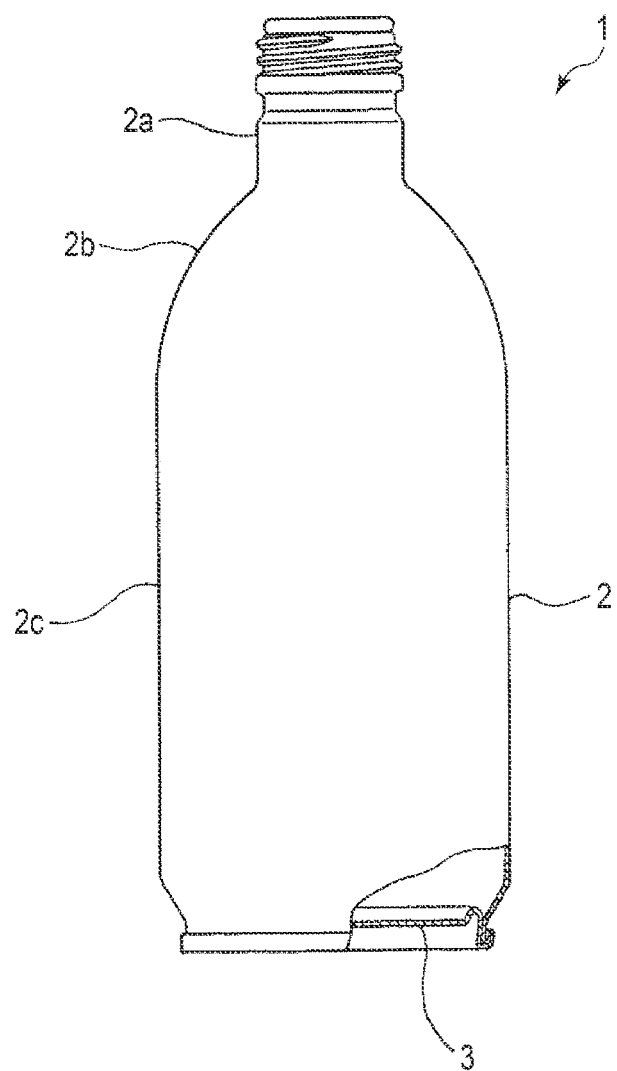
FIG. 1 is a partially cutaway side view of an exemplary aluminum can to be filled with a wine.

The present invention will be described. The description will be given for the appreciation of the invention, and is not intended to limit the invention.

1. Method According to First Aspect

The method according to the first aspect is a method for determining a reference value of a wine for feasibility of filling an aluminum can, and includes the steps of:

acquiring a pH, an alcohol concentration, and a free sulfite concentration for multiple kinds of wines;

calculating a molecular $SO_2$ concentration of each of the multiple kinds of wines from acquired values of the pH, the alcohol concentration, and the free sulfite concentration;

enclosing the multiple kinds of wines into aluminum cans of an identical type, respectively, thereby obtaining multiple kinds of canned wines;

putting the multiple kinds of canned wines in storage and evaluating quality of the canned wines after the storage; and determining an upper limit value of the molecular $SO_2$ concentration based on an evaluation result obtained from the evaluating.

The steps will be described in order.

<Acquisition of pH, Alcohol Concentration, and Free Sulfite Concentration>

In this step, a pH, an alcohol concentration, and a free sulfite concentration are acquired for multiple kinds of wines.

The present method is a method for determining a reference value of a wine (namely, the upper limit value of the molecular $SO_2$ concentration of a wine) that is feasible for filling a specific aluminum can. Accordingly, multiple kinds of wines used for determining the reference value preferably have a wide range of molecular $SO_2$ concentrations. A molecular $SO_2$ concentration is, as will be described, calculated from values of a pH, an alcohol concentration, and a free sulfite concentration. As such, it is desirable that the multiple kinds of wines used for determining the reference value have a wide range of pH values, alcohol concentrations, and free sulfite concentrations. There are no particular limitations on the multiple kinds of wines but, for example, 35 or more kinds of wines, or typically, 35 to 70 kinds of wines may be used. The multiple kinds of wines may preferably be 40 or more kinds of wines, or more preferably be 50 to 70 kinds of wines.

Measurement of pH, measurement of alcohol concentrations, and measurement of free sulfite concentrations may be conducted according to the known methods. Needless to say, each measurement needs to be conducted in such a manner that the same method and the same conditions are employed for all of the multiple kinds of wines.

The pH measurement may utilize, for example, a pH meter for wines. The pH measurement needs to be conducted on the wines having the same temperature since pH varies with wine temperature. For example, the pH measurement may be conducted on the wines having a temperature of 20° C. The alcohol concentration measurement may utilize, for example, an alcohol concentration meter, a hydrometer method, high performance liquid chromatography (HPLC), or gas chromatography. The free sulfite concentration measurement may utilize, for example, a sulfite meter for wines, an aeration distillation and titration method (Rankine's method), or high performance liquid chromatography (HPLC).

<Calculation of Molecular $SO_2$ Concentration>

In this step, the molecular $SO_2$ concentration of each of the multiple kinds of wines is calculated from the acquired values of the pH, the alcohol concentration, and the free sulfite concentration.

The molecular $SO_2$ concentration may be calculated using the following formula.

$$[\text{Molecular SO}_2 \text{ concentration (mg/L)}] = \frac{[\text{Free sulfite concentration (mg/L)}]}{(1 + 10^{(pH - pK\alpha)})} \quad \text{(Formula 1)}$$

$pK\alpha = 1.9499 + a*0.0322 + b*0.01971$ a=Temperature difference from 20° C. (T° C.−20° C.)

b=Difference from 10% vol./vol. alcohol (c %−10)

<Enclosure into Aluminum Cans>

In this step, the multiple kinds of wines are enclosed into aluminum cans of an identical type, respectively, thereby obtaining multiple kinds of canned wines.

As to the aluminum cans, those planned for use in the commercialization of canned wines are adopted. "Aluminum cans of an identical type" refers to aluminum cans of mutually the same material and the same structure.

FIG. 1 shows one example of aluminum cans to be filled with a wine (which may be simply called "aluminum cans" below). An aluminum can 1 shown in FIG. 1 includes a container body 2, a bottom lid 3, and a cap (not shown in the figure). The container body 2 and the bottom lid 3 may together be called an "aluminum can body". The container body 2 integrally includes a spout neck portion 2a, a shoulder portion 2b, and a trunk portion 2c. The bottom lid 3 is integrally seamed and fixed to the container body 2 so as to close the lower opening of the trunk portion 2c. Although not shown in the figure, a pilfer-proof cap, which is a separate component, is attached to the spout neck portion 2a by a well-known roll-on forming process with a capper, so that the pilfer-proof cap will be able to re-seal (re-close) the spout neck portion 2a by screwing. FIG. 1 shows an example of a three-piece type bottle can, but the aluminum can 1 may be a two-piece type bottle can, that is, a bottle can constituted by a container body 2 and a bottom lid 3 formed integrally with each other.

It is preferred that the aluminum can 1 have a resin coating on its inner surfaces (i.e., the inner surface of the container body 2, the inner surface of the bottom lid 3, and the inner surface of the cap) in order to prevent corrosion of the aluminum can. The aluminum can 1 may also have a resin coating on its outer surfaces (i.e., the outer surface of the container body 2, the outer surface of the bottom lid 3, and the outer surface of the cap).

In this step, the aluminum can body is filled with a wine and then subjected to screwing and securing of a separately provided cap according to a known screwing-and-securing step so that a canned wine can be produced.

This step produces a canned wine for each kind of wine, and accordingly, multiple kinds of canned wines are obtained. Preferably, the step adopts the same filling and screwing-and-securing conditions as the production conditions planned for use in the commercialization of canned wines.

<Storage and Quality Evaluation of Canned Wines>

In this step, the multiple kinds of canned wines are put in storage and, after the storage, the quality of the canned wines is evaluated.

The storage may be carried out at a temperature of, for example, 5 to 55° C. and for a period of, for example, 1 to 24 months. In one example, storage at room temperature (i.e., 15 to 25° C.) for 24 months may be carried out. More than one temperature (e.g., various temperatures in a range of 5 to 55° C.) may be adopted as the storage temperature. Also, more than one period (e.g., 1 month, 3 months, 6 months, and 12 months) may be adopted as the storage period. Such a storage test may be conducted in the manner of an accelerated test. Note, however, that the storage test is preferably conducted under the same conditions as the conditions for storing canned wines, for example, conditions during transportation, conditions a store or a user normally uses for storage, and so on. This can increase the reliability of the reference value (i.e. the upper limit value of the molecular $SO_2$ concentration of the wine) determined by the method.

After the storage under the predetermined conditions, the canned wines are subjected to quality evaluation. The quality evaluation may include, for example, evaluation of corrosion resistant characteristics of the aluminum cans. The quality evaluation may preferably include evaluation of corrosion resistant characteristics of the aluminum cans and evaluation of the wine flavor.

The corrosion resistant characteristics of the aluminum cans may be evaluated by cutting open the cans and visually observing the inner surfaces of the cans for the presence of corrosion. The corrosion resistant characteristics of the aluminum cans may also be evaluated by analyzing the amount of aluminum eluted from the aluminum cans and present in the wines. Either one or a combination of visual observation and analytical evaluation may be performed.

The evaluation of the wine flavor may be performed in the manner of a sensory evaluation. The wine flavor may be evaluated by analyzing flavor-affecting indicators of wines, such as acidity, Brix, and flavor components. Either one or a combination of sensory evaluation and analytical evaluation may be performed.

<Determination of Upper Limit Value of Molecular $SO_2$ Concentration>

In this step, the upper limit value of the molecular $SO_2$ concentration is determined based on the evaluation result obtained from the quality evaluation described above.

More specifically, the upper limit value of the molecular $SO_2$ concentration may be determined based on the molecular $SO_2$ concentration of a wine that showed a good result in the above quality evaluation and/or the molecular $SO_2$ concentration of a wine that showed a poor result in the quality evaluation.

For example, the upper limit value of the molecular $SO_2$ concentration may be set to 80 to 90% of the value of the highest molecular $SO_2$ concentration among the wines with good evaluation results. Typically, the upper limit value of the molecular $SO_2$ concentration may be set to 90% of the value of the highest molecular $SO_2$ concentration among the wines with good evaluation results. As one example, in an instance where the highest molecular $SO_2$ concentration among the wines with good evaluation results is 4.8 [mg/L], the upper limit value of the molecular $SO_2$ concentration may be set to 4.3 [mg/L].

<Additional Steps>

The method according to the first aspect above may further include:

acquiring a chloride ion concentration for the multiple kinds of wines; and determining an upper limit value of the chloride ion concentration within a range not exceeding 350 mg/L based on the evaluation result obtained from the evaluating.

In other words, the method may include the steps of:

acquiring a pH, an alcohol concentration, a free sulfite concentration, and a chloride ion concentration for multiple kinds of wines;

calculating a molecular $SO_2$ concentration of each of the multiple kinds of wines from acquired values of the pH, the alcohol concentration, and the free sulfite concentration;

enclosing the multiple kinds of wines into aluminum cans of an identical type, respectively, thereby obtaining multiple kinds of canned wines;

putting the multiple kinds of canned wines in storage and evaluating quality of the canned wines after the storage; and determining an upper limit value of the molecular $SO_2$ concentration and also determining, within a range not exceeding 350 mg/L, an upper limit value of the chloride ion concentration, based on an evaluation result obtained from the evaluating.

This method determines, as a reference value of a wine that is feasible for filling an aluminum can, an upper limit value of the concentration of chloride ions in the wine in addition to an upper limit value of the concentration of molecular $SO_2$ in the wine. As such, it is possible to carry out the method in the same manner as described above, except for measuring a chloride ion concentration and determining an upper limit value of the chloride ion concentration.

Measurement of a chloride ion concentration may be conducted using, for example, a potentiometric titration method, a precipitation titration method (Mohr's method), or ion chromatography. Needless to say, the chloride ion concentration measurement needs to be conducted in such a manner that the same method and the same conditions are employed for all of the multiple kinds of wines.

The upper limit value of the chloride ion concentration is determined based on the result of the quality evaluation. More specifically, the upper limit value of the chloride ion concentration may be determined based on the chloride ion concentration of a wine that showed a good result in the quality evaluation and/or the chloride ion concentration of a wine that showed a poor result in the quality evaluation. Note, However, that the upper limit value of the chloride ion concentration is determined within a range not exceeding 350 mg/L. The reason why the upper limit of the chloride ion concentration should be determined within a range not exceeding 350 mg/L is that the concentration of chloride ions in a wine not exceeding 350 mg/L is desirable from the viewpoint of corrosion of aluminum cans and deterioration of wine flavor.

For example, the upper limit value of the chloride ion concentration may be set to 90% of the value of the highest chloride ion concentration among the wines with good evaluation results, and if the thus set value is 350 mg/L or lower, this value may be adopted as the upper limit value of the chloride ion concentration. If the set value exceeds 350 mg/L, then 350 mg/L may be adopted as the upper limit value of the chloride ion concentration.

The method determines the upper limit value of the chloride ion concentration in addition to the upper limit value of the molecular $SO_2$ concentration. Therefore, when the two upper limit values determined by this method are used, and the feasibility of filling an aluminum can with a subject wine is checked in accordance with the below described method according to the second aspect, a subject wine having a molecular $SO_2$ concentration and a chloride ion concentration equal to or lower than the respective upper limit values can be determined to be a wine that is feasible for filling the aluminum can. In other words, if either the molecular $SO_2$ concentration or the chloride ion concentration of a subject wine exceeds the corresponding upper limit value, this subject wine can be excluded from the wines that are feasible for filling the aluminum can.

2. Method According to Second Aspect

The method according to the second aspect is a method for checking feasibility of filling an aluminum can with a wine, and includes the steps of:
  acquiring a pH, an alcohol concentration, and a free sulfite concentration for a subject wine intended to be enclosed in an aluminum can used in the method according to the first aspect;
  calculating a molecular $SO_2$ concentration of the subject wine from acquired values of the pH, the alcohol concentration, and the free sulfite concentration; and
  excluding the subject wine from wines that are feasible for filling the aluminum can used in the method according to the first aspect if the calculated molecular $SO_2$ concentration exceeds the upper limit value of the molecular $SO_2$ concentration determined by the method according to the first aspect.

The method according to the second aspect checks whether or not a subject wine is feasible for filling a subject aluminum can based on the reference value or values determined by the method according to the first aspect (more specifically, the upper limit value of the molecular $SO_2$ concentration, or preferably, the upper limit value of the molecular $SO_2$ concentration and the upper limit value of the chloride ion concentration).

The steps will be described in order.

<Acquisition of pH, Alcohol Concentration, and Free Sulfite Concentration>

In this step, a pH, an alcohol concentration, and a free sulfite concentration are acquired for a subject wine which is intended to fill the aluminum can used in the method according to the first aspect.

The subject wine is, for example, a wine which is planned to be enclosed in the aluminum can used in the method according to the first aspect for sale. The "aluminum can used in the method according to the first aspect" refers to an aluminum can of the same or identical type as the aluminum can used in the method according to the first aspect, that is, an aluminum can constituted by the same material and having the same structure as the aluminum can used in the method according to the first aspect. This step may be performed in the same manner as the step of "acquiring a pH, an alcohol concentration, and a free sulfite concentration" in the method according to the first aspect.

<Calculation of Molecular $SO_2$ Concentration>

In this step, the molecular $SO_2$ concentration of the subject wine is calculated from the acquired values of the pH, the alcohol concentration, and the free sulfite concentration. This step may be performed in the same manner as the step of "calculating a molecular $SO_2$ concentration" in the method according to the first aspect.

<Determination of Wine Having Filling Feasibility>

In this step, the subject wine is excluded from wines that are feasible for filling the aluminum can used in the method according to the first aspect if the calculated molecular $SO_2$ concentration exceeds the upper limit value of the molecular $SO_2$ concentration determined by the method according to the first aspect. A subject wine not excluded by this step may be determined to be a wine that is feasible for filling the aluminum can used in the method according to the first aspect.

In other words, it is possible with this step to determine a subject wine to be a wine that is feasible for filling the aluminum can used in the method according to the first aspect if the calculated molecular $SO_2$ concentration is equal to or lower than the upper limit value of the molecular $SO_2$ concentration determined by the method according to the first aspect.

<Additional Steps>

The method according to the second aspect above may further include:
  acquiring a chloride ion concentration for the subject wine; and
  excluding the subject wine from wines that are feasible for filling the aluminum can used in the method according to the first aspect if the calculated molecular $SO_2$ concentration exceeds the upper limit value of the molecular $SO_2$ concentration determined by the method according to the first aspect or if the acquired chloride ion concentration exceeds the upper limit value of the chloride ion concentration determined by the method according to the first aspect.

In other words, the method may include the steps of:
  acquiring a pH, an alcohol concentration, a free sulfite concentration, and a chloride ion concentration for a subject wine intended to be enclosed in an aluminum can used in the method according to the first aspect;
  calculating a molecular $SO_2$ concentration of the subject wine from acquired values of the pH, the alcohol concentration, and the free sulfite concentration; and
  excluding the subject wine from wines that are feasible for filling the aluminum can used in the method according to the first aspect if the calculated molecular $SO_2$ concentration exceeds the upper limit value of the molecular $SO_2$ concentration determined by the method according to the first aspect or if the acquired chloride ion concentration exceeds the upper limit value of the chloride ion concentration determined by the method according to the first aspect.

In this method, whether or not a subject wine is feasible for filling a subject aluminum can is checked using, as a reference value of a wine that is feasible for filling an aluminum can, an upper limit value of the concentration of chloride ions in the wine in addition to an upper limit value of the concentration of molecular $SO_2$ in the wine.

More specifically, in this step, a subject wine is excluded from wines that are feasible for filling the aluminum can used in the method according to the first aspect if the calculated molecular $SO_2$ concentration exceeds the upper limit value of the molecular $SO_2$ concentration determined by the method according to the first aspect or if the acquired chloride ion concentration exceeds the upper limit value of the chloride ion concentration determined by the method according to the first aspect. A subject wine not excluded by this step may be determined to be a wine that is feasible for filling the aluminum can used in the method according to the first aspect.

In other words, it is possible with this step to determine a subject wine to be a wine that is feasible for filling the aluminum can used in the method according to the first aspect if the calculated molecular $SO_2$ concentration is equal to or lower than the upper limit value of the molecular $SO_2$ concentration determined by the method according to the first aspect and if the acquired chloride ion concentration is equal to or lower than the upper limit value of the chloride ion concentration determined by the method according to the first aspect.

3. Method According to Third Aspect

The method according to the third aspect is a method for producing an aluminum-canned wine, and includes the step of enclosing a subject wine determined to have a filling feasibility by the method according to the second aspect into an aluminum can of an identical type to the aluminum can used in the method according to the first aspect.

The method according to the third aspect encloses only the subject wine determined to have a filling feasibility based on the check result from the method according to the second aspect into the aluminum can. The "aluminum can of an identical type to the aluminum can used in the method according to the first aspect" refers to an aluminum can constituted by the same material and having the same structure as the aluminum can used in the method according to the first aspect. The enclosure of the subject wine into the aluminum can may be performed in the same manner as the step of "enclosure into aluminum cans" in the method according to the first aspect.

4. Effects

As described above, with the method according to the first aspect, a reference value of a wine (namely, the upper limit value of the molecular $SO_2$ concentration of a wine) having a filling feasibility can be determined in advance for each aluminum can. With the method according to the second aspect, whether or not filling a subject aluminum can with a subject wine is feasible (that is, whether or not corrosion resistance is guaranteed if the subject wine is stored in the subject aluminum can) can be checked based on the reference value or values determined by the method according to the first aspect, without carrying out a storage test. With the method according to the third aspect, aluminum-canned wines can be produced for the subject wines determined to have a filling feasibility by the method according to the second aspect. Therefore, according to the present invention, a time required for the commercialization of aluminum-canned wines can be reduced while ensuring the corrosion resistant characteristics of aluminum cans.

5. Preferred Aluminum Cans

A description will be given of aluminum cans which are preferably used in the methods described above (i.e., the method according to the first aspect, the method according to the second aspect, and the method according to the third aspect). One preferred aluminum can is a bottle can (cf. FIG. 1) having a below described resin coating on its inner surface for the prevention of aluminum can corrosion.

More specifically, a preferred aluminum can includes an aluminum sheet, a resin film provided on a surface of the aluminum sheet which faces an internal space of the aluminum can, and an adhesive layer interposed between the aluminum sheet and the resin film and bonding them together, wherein:
the resin film includes a first resin layer as a topmost layer and a second resin layer containing a dimer acid-copolymerized polyester resin, and
at least one of the resin layers constituting the resin film, and/or the adhesive layer contains calcium carbonate.

Figure 2:
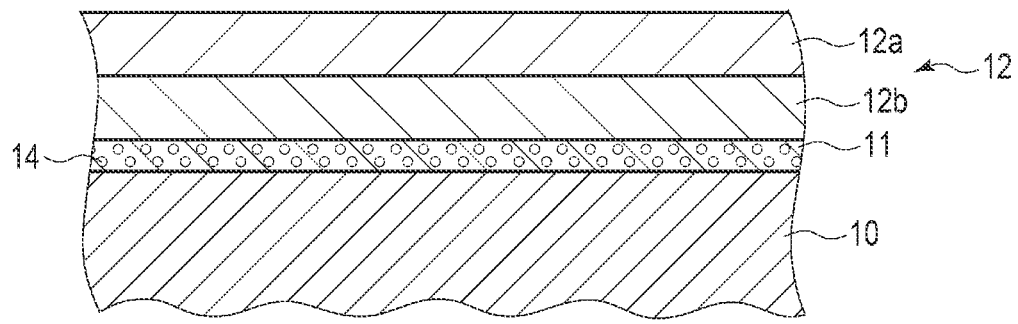
FIG. 2 is a sectional view of an exemplary layer structure of the aluminum can to be filled with a wine.
Figure 3:
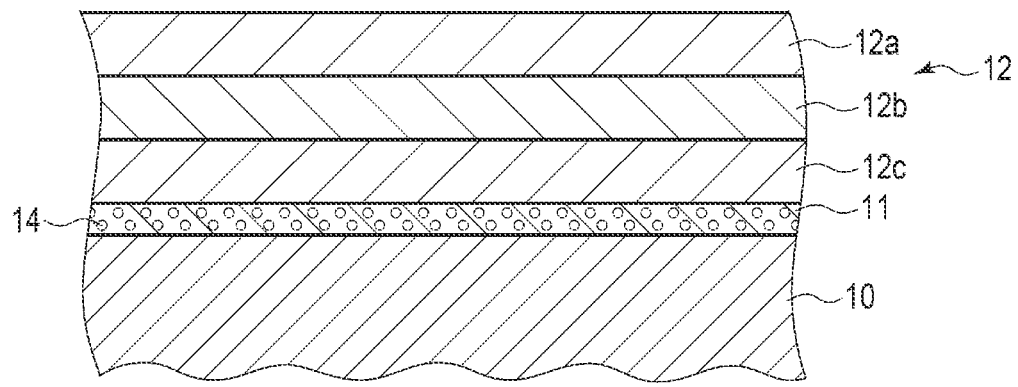
FIG. 3 is a sectional view of another exemplary layer structure of the aluminum can to be filled with a wine.

An example of such a layer structure of the aluminum can is shown in FIG. 2, and another example of the layer structure of the aluminum can is shown in FIG. 3.

The aluminum can having the layer structure shown in FIG. 2 (which may be called an "aluminum can according to the first embodiment") includes an aluminum sheet 10, a resin film 12 provided on a surface of the aluminum sheet 10 which faces an internal space of the aluminum can, and an adhesive layer 11 interposed between the aluminum sheet 10 and the resin film 12 and bonding them together, wherein:
the resin film 12 is a laminate film having a two-layered structure constituted by a first resin layer 12a as a topmost layer and a second resin layer 12b containing a dimer acid-copolymerized polyester resin, and
the adhesive layer 11 contains calcium carbonate 14.

The aluminum can having the layer structure shown in FIG. 3 (which may be called an "aluminum can according to the second embodiment") includes an aluminum sheet 10, a resin film 12 provided on a surface of the aluminum sheet 10 which faces an internal space of the aluminum can, and an adhesive layer 11 interposed between the aluminum sheet 10 and the resin film 12 and bonding them together, wherein:
the resin film 12 is a laminate film having a three-layered structure constituted by a first resin layer 12a as a topmost layer, a second resin layer 12b as an intermediate layer containing a dimer acid-copolymerized polyester resin, and a third resin layer 12c as an outermost layer facing the adhesive layer 11, and
the adhesive layer 11 contains calcium carbonate 14.

The aluminum can according to the first embodiment is the same as the aluminum can according to the second embodiment except that it omits the third resin layer 12c included in the aluminum can according to the second embodiment. Hence, the description will concentrate on the aluminum can according to the second embodiment.

5-1. Resin Film 12

In the second embodiment, the resin film 12 provided on the surface of the aluminum sheet 10 which faces an internal space of the can is a laminate film having a three-layered structure. As shown in the figure, this three-layered laminate film is constituted by the first resin layer 12a, the second resin layer 12b, and the third resin layer 12c. More specifically, the first resin layer 12a may be a resin film consisting mainly of (i.e., containing 50 mass % or more of) an isophthalic acid-copolymerized polyester resin that contains 3 to 15 mol % of isophthalic acid with respect to the total acid content in the first resin layer 12a. The second resin layer 12b may be a resin film consisting mainly of (i.e., containing 50 mass % or more of) a dimer acid-copolymerized polyester resin that contains 5 to 50 mol % of dimer acid with respect to the total acid content in the second resin layer 12b. The third resin layer 12c may be a resin film consisting mainly of (i.e., containing 50 mass % or more of) an isophthalic acid-copolymerized polyester resin containing 3 to 15 mol % of isophthalic acid with respect to the total acid content in the third resin layer 12c. The first resin layer 12a, the second resin layer 12b, and the third resin layer 12c each have a thickness of, for example, 3 to 10 µm. It is preferable for the resin film 12 to have a dimer acid ratio of 3 to 30 mol % to the total acid content in the entire film.

Because of the inclusion of the dimer acid-copolymerized polyester resin in this laminate film of a three-layered structure, the resin film 12 can be made flexible. Use of such a resin film 12 having a good flexibility realizes an excellent film formability, and prevents occurrences of film rupture (hair) and scraping (galling) during the drawing and ironing processes in the manufacturing of cans. Further, use of the resin film 12 can avoid breakage of film surfaces and suppress corrosion of aluminum cans, even in the event of dropping of cans or an external impact (dent) on cans after the cans have been provided as finished products with contents enclosed therein. That is, the quality associated with the inner surface side of the aluminum cans can be assured.

Also, although the second resin layer 12b containing the dimer acid-copolymerized polyester resin may be sticky at high temperature and flexible and easily damaged at room temperature, the three-layered laminate film ensures that the second resin layer 12b is sandwiched between the first resin layer 12a and the third resin layer 12c, each of which contains the isophthalic acid-copolymerized polyester resin. Thus, improved usability for the resin film 12 can be realized. Put another way, the first resin layer 12a and the third resin layer 12c do not become sticky even at high temperature and are relatively robust at room temperature, and therefore, they will not cause a problem of winding around a high-temperature stretching roll during the film formation, nor will they become damaged at the time of conveyance during the formation of aluminum cans, etc. Besides, problems such as winding around a stretching roll and damage at the time of conveyance for aluminum cans are often solvable by special measures such as subjecting the component located at the source of trouble to a surface treatment, or by other measures such as reduction of production speed. In these cases, the first resin layer 12a and the third resin layer 12c may be omitted according to the technical measures taken in production.

While not shown in the figures, a resin film may be provided on the surface of the aluminum sheet 10 which faces an external space (an exterior) of the can. This outer-surface-side resin film may be, for example, a blended resin containing polybutylene terephthalate and isophthalic acid-copolymerized polyethylene terephthalate (PBT/copolymerized PET). The outer-surface-side resin film has a thickness of, for example, 5 to 20 µm.

5-2. Adhesive Layer 11

The resin film 12 described above may be bonded to the aluminum sheet 10 via the adhesive layer 11. The adhesive layer 11 may be, for example, an adhesive made of a thermosetting epoxy resin. It is preferable for the adhesive layer 11 not to contain a bisphenol-A epoxy resin. A bisphenol-A epoxy resin is suspected to be an endocrine disrupter substance. Thus, the absence of a bisphenol-A epoxy resin is desirable for the sake of reliably avoiding elution of any bisphenol-A epoxy resin into the contents of can containers. In order to enhance the adhesion properties without containing a bisphenol-A epoxy resin, it is preferable to, for example, set the content ratio (mass ratio) of a polyester resin to a phenol resin to be [10 to 40]:[0 to 20]. The adhesive layer 11 has a thickness, for example, of 2 to 20 µm.

In the first and second embodiments, the calcium carbonate 14 is contained in the form of particles in the adhesive layer 11. The calcium carbonate 14 functions as an acid scavenger which reacts with sulfite. The calcium carbonate 14 is thus able to prevent the sulfite contained in wines from passing through the resin film 12 and reaching the aluminum sheet 10. This consequently allows for the prevention of corrosion of aluminum cans and also the prevention of deterioration of wine flavor due to hydrogen sulfide generated by the reaction between sulfite and aluminum.

The particles of the calcium carbonate 14 have an average particle size of, for example, 0.01 to 4.0 µm, preferably 0.01 to 0.1 µm. The calcium carbonate 14 may be added in an amount of, for example, 5 to 50 parts by mass with respect to the adhesive resin being 100 parts by mass. A too small amount of the added calcium carbonate could incur degradation of the above described effects, and a too large amount of the added calcium carbonate could incur degradation of the formability of the resin film 12.

It is preferable that the calcium carbonate 14 be contained in the adhesive layer 11. This enables the calcium carbonate 14 to effectively catch the sulfite contained in wines. The calcium carbonate 14 may also be contained in any of the layers in the resin film 12, in addition to being contained in the adhesive layer 11. In other instances, the calcium carbonate 14 may be contained in any of the layers in the resin film 12, instead of being contained in the adhesive layer 11. In this case, it is preferable that the resin film 12 be constituted by multiple layers, and that the calcium carbonate 14 be contained in a layer different from the topmost layer. With the calcium carbonate 14 contained in a layer different from the topmost layer of the resin film 12, it is possible to eliminate the risk of creating micro defects during the formation of aluminum cans.

5-3. Details of Resin Film 12

Details of the resin film 12 according to the second embodiment will be described.

<First Resin Layer 12a>

The first resin layer 12a may be a resin film containing, at a content of, e.g., 50 to 100 mass %, an isophthalic acid-copolymerized polyester resin that contains 3 to 15 mol % of isophthalic acid with respect to the total acid content in the first resin layer 12a. Such a resin film has a property of not being sticky at approximately 130° C.

The isophthalic acid-copolymerized polyester resin includes, for example, a dicarboxylic acid unit containing 85 to 97 mol % of a terephthalic acid component and 15 to 3 mol % of an isophthalic acid component, and a diol unit containing 90 mol % or more of an ethylene glycol component. That is, the isophthalic acid-copolymerized polyester resin consists, for example, mainly of ethylene terephthalate in which 3 to 15 mol % of the isophthalic acid component is copolymerized. Copolymerization of the isophthalic acid component can endow the film with flexibility. Accordingly, it is possible to prevent occurrences of tiny cracks on the surfaces of aluminum cans during their formation.

The isophthalic acid-copolymerized polyester resin may also contain a dicarboxylic acid unit other than the terephthalic acid component and the isophthalic acid component within a range that does not impair the adequacy of lamination to the aluminum sheet and the properties of the aluminum cans, for example, within a range of 10 mol % or less. Examples of such a dicarboxylic acid unit include succinic acid, adipic acid, azelaic acid, sebacic acid, 1,4-naphthalene dicarboxylic acid, 4,4'-biphenyl dicarboxylic acid, 1,12-dodecanoic acid, 1,2-cyclohexane dicarboxylic acid, 1,3-cyclohexane dicarboxylic acid, 1,4-cyclohexane dicarboxylic acid, and so on, any one of which may be used independently or two or more of which may be used in combination.

The isophthalic acid-copolymerized polyester resin may contain a diol unit other than the ethylene glycol component within a range of 10 mol % or less. Examples of such a diol unit include aliphatic diols such as diethylene glycol, triethylene glycol, 1,2-propanediol, 1,3-propanediol, 1,4-butanediol, 1,5-pentanediol, 1,6-hexanediol, and neopentyl glycol, alicyclic diols such as 1,4-cyclohexanedimethanol and 1,4-cyclohexanediethanol, and so on, any one of which may be used independently or two or more of which may be used in combination.

The isophthalic acid-copolymerized polyester resin is obtained by inducing an esterification reaction of the above described dicarboxylic acid component with the above described diol component by a known method. For example, this method may be a method of using the dicarboxylic acid component that has a methyl group added to its terminal as a starting material, and causing an ester exchange reaction with the diol component through addition of a catalyst, or a method of using the dicarboxylic acid component without a modified terminal as a starting material and causing an esterification reaction directly with the diol component. For other instances, a commercially available isophthalic acid-copolymerized polyethylene terephthalate resin may be employed, examples of which include IP121B, PIFG8, and PIFG10 (all from Bell Polyester Products, Inc.). While it is not a particular requirement for the isophthalic acid-copolymerized polyester resin to have a specific limiting viscosity, its limiting viscosity is preferably 0.7 to 0.9.

The isophthalic acid-copolymerized polyester resin described above may be used alone in the form of a film, or may be used together with a single polyester resin or multiple polyester resins, e.g., a polyethylene terephthalate resin, a polybutylene terephthalate resin, a polytrimethylene terephthalate resin, etc., which may be blended in a proportion of less than 50 mass % with respect to the isophthalic acid-copolymerized polyester resin.

<Second Resin Layer 12b>

The second resin layer 12b may be a resin film containing a dimer acid-copolymerized polyester resin at a content of, for example, 50 to 100 mass %.

The dimer acid-copolymerized polyester resin, for example, includes:
  (A) 50 to 93 mass % of an ester oligomer which contains
    (a1) a dicarboxylic acid unit containing 70 mol % or more of a terephthalic acid component and
    (a2) a diol unit containing 70 mol % or more of an ethylene glycol component, and
    which has a number-average molecular weight of 700 or less; and
  (B) 7 to 50 mass % of a polyester polyol which contains
    (b1) a hydrogenated dimer acid unit and
    (b2) a 1,4-butanediol unit, and
    which has a number-average molecular weight of 1500 to 3000.

(Ester Oligomer (A))

In the above dimer acid-copolymerized polyester resin, the dicarboxylic acid unit (a1) contains 70 mol % or more of a terephthalic acid unit. The entirety of the dicarboxylic acid unit may be a terephthalic acid unit. Or, a dicarboxylic acid unit other than the terephthalic acid unit may be contained within a range that does not impair the adequacy of lamination to the aluminum sheet and the properties of the aluminum cans for formation, and within a range of less than 30 mol %. Examples of this dicarboxylic acid component other than the terephthalic acid unit include isophthalic acid, succinic acid, adipic acid, azelaic acid, sebacic acid, 1,4-naphthalene dicarboxylic acid, 4,4'-biphenyl dicarboxylic acid, 1,12-dodecanoic acid, 1,2-cyclohexane dicarboxylic acid, 1,3-cyclohexane dicarboxylic acid, 1,4-cyclohexane dicarboxylic acid, and so on, any one of which may be used independently or two or more of which may be used in combination. Among these, for example, isophthalic acid may be suitably used within a range of about 1 to 30 mol %, for enhancing the dent resistant characteristics (i.e., properties of avoiding breakage of film surfaces so that corrosion of an aluminum sheet does not easily occur, even if an external shock (dent) is applied) of the aluminum cans having a film coating.

In the above dimer acid-copolymerized polyester resin, the diol unit (a2) contains 70 mol % or more of an ethylene glycol unit. The entirety of the diol unit may be an ethylene glycol unit. Or, a diol component other than the ethylene glycol unit may be contained within a range of less than 30 mol %. Examples of the diol component other than the ethylene glycol unit include propylene glycol, butanediol, neopentyl glycol, diethylene glycol, cyclohexane dimethanol, and so on, any one of which may be used independently or two or more of which may be used in combination.

In the dimer acid-copolymerized polyester resin described above, the number-average molecular weight of the ester oligomer (A) is 700 or less, preferably 300 to 700. By conducting copolymerization using the ester oligomer (A) of the number-average molecular weight of 700 or less, a copolymerized polyester resin in which the polyester polyol (B) is randomly bonded within the polymer chains and which has a clear appearance is obtained. The copolymerized polyester resin thus obtained has good compatibility with other resins, and therefore allows for stable film formation without incurring problems such as occurrence of a surging phenomenon (unstable discharge phenomenon) when being subjected to melt-extrusion after blending with other resins.

On the other hand, if an ester oligomer having a number-average molecular weight of more than 700, for example, around 1000, is used instead, the polymerization reaction reaches a termination point in the course of copolymerization with the polyester polyol (B), and as such, cannot produce a high-viscosity copolymerized polyester resin having a limiting viscosity of about 0.7 to 0.9. Also, use of polyester having a number-average molecular weight of more than 5000 can produce a high-molecular copolymerized polyester resin without causing the polymerization stop phenomenon, but the obtained copolymerized polyester resin will be an -(A)-(B)-type block copolymer because of the large molecular weight of the ester (A) unit, and the appearance of the resin will be clouded due to phase separations. Furthermore, since such a block copolymer has poor compatibility with other resins, the problem of a surging phenomenon (unstable discharge phenomenon) occurring at the time of melt-extrusion, and sheet or film formation not being permitted, exists.

The ester oligomer (A) is obtained by inducing an esterification reaction of the dicarboxylic acid component (a1), consisting mainly of terephthalic acid, with the diol component (a2), consisting mainly of ethylene glycol, by a known method. For example, this method may be a method of acquiring the oligomer by using the dicarboxylic acid component (a1) that has a methyl group added to its terminal as a starting material and causing an ester exchange reaction with the diol component (a2) through addition of a catalyst, or a method of acquiring the oligomer by using the dicarboxylic acid component (a1) without a modified terminal as a starting material and causing an esterification reaction directly with the diol component (a2).

It is preferable in the production of the ester oligomer (A) that, after a predetermined esterification rate is reached at a reaction temperature of, for example, 230 to 250° C., an input of 3 to 10 mass % of diol (ethylene glycol) with respect to the total oligomer obtained be provided to the system so that depolymerization reaction takes place for about 30 minutes to 1 hour, with the internal temperature kept at 230 to 250° C. By carrying out the depolymerization reaction using diol (ethylene glycol) after the esterification reaction, the number-average molecular weight of the ester oligomer (A) can be adjusted to 700 or less. If, on the other hand, the depolymerization reaction is not carried out, the number-average molecular weight of the ester oligomer resulting under normal conditions will be high and exceed 700. Even in the case of omitting the depolymerization reaction, it is possible to regulate the number-average molecular weight to 700 or less by setting a molar ratio of the diol component with respect to the dicarboxylic acid component to a high range of 1.25 to 1.60; nevertheless, the number-average molecular weight would exceed 700 if the molar ratio of the diol component falls below 1.25.

(Polyester Polyol (B))

In the above dimer acid-copolymerized polyester resin, the polyester polyol (B) has a dicarboxylic acid unit constituted by the hydrogenated dimer acid unit (b1). The dimer acid refers to, for example, a dicarboxylic acid compound having 36 carbon atoms and obtained by dimerizing an unsaturated fatty acid having 18 carbon atoms such as oleic acid or linoleic acid. The hydrogenated dimer acid refers to a dimer acid in which unsaturated double bonds remaining after the dimerization have been saturated through hydrogenation, and the dicarboxylic acid unit of the polyester polyol (B) is constituted by such a hydrogenated dimer acid unit (b1). Note that the hydrogenated dimer acid is normally obtained as a mixture of compounds of a linear structure, compounds of a branched structure, compounds of an alicyclic structure, etc., and the ratio of their contents varies depending on the production processes. However, the content ratio in the context of the present invention is not particularly limited. The polyester polyol (B) also has a diol unit constituted by the 1,4-butanediol unit (b2). Here, the terminals of the polyester polyol (B) are all hydroxyl groups from the 1,4-butanediol unit (b2).

The polyester polyol (B) has a number-average molecular weight of 1500 to 3000, preferably 1800 to 2500. Having an average molecular weight in this range gives an excellent reactivity at the time of copolymerization, and also allows the obtained copolymerized polyester resin to demonstrate excellent performance as a film for coating a metal sheet. On the other hand, if the average molecular weight is less than 1500, while good reactivity at the time of copolymerization will still be observed, the obtained copolymerized polyester resin tends to provide poor dent resistant characteristics of the aluminum cans having a film coating. If the average molecular weight exceeds 3000, the reactivity at the copolymerization becomes poor, and a copolymerized polyester resin having a desired molecular weight will not be obtained.

The polyester polyol (B) can be obtained by inducing an esterification reaction of the hydrogenated dimer acid unit (b1) with the 1,4-butanediol unit (b2) by a known method, but this requires adjustment of the molar ratio for the reaction so that the terminal turns to a hydroxyl group. In another instance, a commercial product may be employed as the polyester polyol (B). For example, there exists a commercially available product named Priplast3199 (manufactured by Croda) as the polyester polyol including a hydrogenated dimer acid and 1,4-butanediol and having a number-average molecular weight of 2200. Other commercially available polyester polyol products are Priplast3162, 3192, 3196, 2101, and 2104 (all from Croda), etc.

(Copolymerized Polyester Resin)

The dimer acid-copolymerized polyester resin described above can be obtained by inducing the copolymerization reaction of 50 to 93 mass % of the ester oligomer (A) with 7 to 50 mass % of the polyester polyol (B). Here, the polyester polyol (B) accounts for a content of 7 to 50 mass %, preferably 15 to 35 mass %, of the entire polymer. The content of the polyester polyol (B) being within this range provides excellent copolymerization reactivity, and also particularly good dent resistant characteristics of the aluminum cans having a film coating. Moreover, since the copolymerized polyester resin is obtained with the polyester polyol (B) randomly bonded within its polymer chains, it has a clear and colorless, or clear and slightly yellow, appearance. On the other hand, if the content of the polyester polyol (B) is less than 7 mass %, the dent resistant characteristics of the aluminum cans having a film coating could be degraded. Also, if the content of the polyester polyol (B) exceeds 50 mass %, the copolymerization reactivity becomes poor and the obtained copolymerized polyester resin could show a whitish appearance as involving phase separations of the polyester polyol (B).

The copolymerization reaction between the ester oligomer (A) and the polyester polyol (B) may be carried out by a conventionally known method. For example, a reaction system obtained by mixing each component is gradually depressurized from atmospheric pressure to a highly vacuum condition of 133.3 Pa or below, and the series of reactions may be carried out under this condition. Desirably, the temperature during the reactions should be controlled to between 250° C. and 270° C. If the temperature exceeds 270° C., a decrease in viscosity due to deterioration may occur in the latter stage of the copolymerization reaction, and if the temperature is below 250° C., the copolymerization reaction may not proceed. The copolymerization reaction may employ a polymerization catalyst such as antimony trioxide, germanium dioxide, or a titanium compound, and it is preferable to use, among these, the titanium compound such as tetrabutyl titanate or tetraisopropoxy titanate from the viewpoint of reactivity, safety, and cost. The dimer acid-copolymerized polyester resin described above is not particularly limited to a specific limiting viscosity, but preferably has a limiting viscosity of 0.7 to 0.9.

Another method for obtaining the dimer acid-copolymerized polyester resin may be to esterify dicarboxylic acids containing 70 to 97 mol % of a terephthalic acid component and 30 to 3 mol % of a dimer acid component with diols containing 90 mol % or more of an ethylene glycol component by a known method.

The dimer acid-copolymerized polyester resin may also contain a dicarboxylic acid unit other than the terephthalic acid component and the dimer acid component within a range that does not impair the adequacy of lamination to the aluminum sheet and the properties of the aluminum cans, for example, within a range of 10 mol % or less. Examples of such a dicarboxylic acid unit include isophthalic acid, succinic acid, adipic acid, azelaic acid, sebacic acid, 1,4-naphthalene dicarboxylic acid, 4,4'-biphenyl dicarboxylic acid, 1,12-dodecanoic acid, 1,2-cyclohexane dicarboxylic acid, 1,3-cyclohexane dicarboxylic acid, 1,4-cyclohexane dicarboxylic acid, and so on, any one of which may be used independently or two or more of which may be used in combination.

Also, the dimer acid-copolymerized polyester resin may contain a diol unit other than the ethylene glycol component within a range of 10 mol % or less. Examples of such a diol unit include aliphatic diols such as diethylene glycol, triethylene glycol, 1,2-propanediol, 1,3-propanediol, 1,4-butanediol, 1,5-pentanediol, 1,6-hexanediol, and neopentyl glycol, alicyclic diols such as 1,4-cyclohexanedimethanol and 1,4-cyclohexanediethanol, and so on, any one of which may be used independently or two or more of which may be used in combination.

The dimer acid-copolymerized polyester resin described above may be used alone in the form of a film, or may be blended with one or more other polyester resins for use. Such other polyester resins are, for example, a polyethylene terephthalate resin, an isophthalic acid-copolymerized polyester resin, a polybutylene terephthalate resin, a polytrimethylene terephthalate resin, and so on, and any one of them may be blended alone, or multiple of them may be blended together, in a proportion of less than 50 mass % with respect to the dimer acid-copolymerized polyester resin.

<Third Resin Layer 12c>

The third resin layer 12c may be a resin film containing, at a content of, e.g., 50 to 100 mass %, an isophthalic acid-copolymerized polyester resin that contains 3 to 15 mol % of isophthalic acid with respect to the total acid content in the third resin layer 12c. The third resin layer 12c may have the same composition as the first resin layer 12a.

It is possible to add, to the copolymerized polyester resins of the first resin layer 12a, the second resin layer 12b, and the third resin layer 12c, a metallic salt such as magnesium acetate, calcium acetate, or magnesium chloride as an additive in order to gain the property of stable electrostatic adhesion to a cooling roll used in the formation of a melt-extruded film. In addition, it is also possible to mix an appropriate amount of inert particles such as silica, alumina, calcium carbonate, or titanium dioxide as an anti-blocking agent for a film roll, such inert particles preferably having an average particle size of 1.0 to 4.0 μm. The average particle size of less than 1.0 μm would incur degradation of the anti-blocking property, and the average particle size of greater than 4.0 μm would cause dropping-off of the particles due to abrasion, or film breakage during the stretching process.

The copolymerized polyester resins of the first resin layer 12a, the second resin layer 12b, and the third resin layer 12c may also contain, as needed, an additive such as a coloring pigment, wax, a heat stabilizer, an antioxidant, or an ultraviolet absorber. The antioxidant may be a hindered phenol-based antioxidant, a phosphorus-based antioxidant, a sulfur-based antioxidant, etc., but the hindered phenol-based antioxidant is particularly preferable. More than one type of such antioxidants may be added in combination, and the content of the antioxidant is preferably 100 to 5000 ppm.

<Laminate Film>

The resin film 12 can be obtained by laminating the copolymerized polyester resins of the first resin layer 12a, the second resin layer 12b, and the third resin layer 12c by a known method. For example, this method may be a method of feeding the copolymerized polyester resin of the first resin layer 12a, that of the second resin layer 12b, and that of the third resin layer 12c into respective, different extruders and co-extruding them from a single die simultaneously (co-extrusion laminating). Or, the method may be a method of preparing a film of the first resin layer 12a (or the third resin layer 12c) in advance by a T-die process or an inflation process, melt-extruding the copolymerized polyester resin of the second resin layer 12b onto the surface of this film being conveyed, solidifying the resulting product by cooling, melt-extruding the copolymerized polyester resin of the third resin layer 12c (or the first resin layer 12a) onto the surface of the obtained two-layered film being conveyed, and solidifying the resulting product by cooling (extrusion laminating). The resin film 12 is not particularly limited to a specific thickness, but the sum of the thicknesses of the first resin layer 12a, the second resin layer 12b, and the third resin layer 12c is preferably 9 to 30 μm.

6. Preferred Embodiments 6-1. Method for Determining Reference Value of Wine for Feasibility of Filling Aluminum can <A1> A method for determining a reference value of a wine for feasibility of filling an aluminum can, the method including:
  acquiring a pH, an alcohol concentration, and a free sulfite concentration for multiple kinds of wines;
  calculating a molecular $SO_2$ concentration of each of the multiple kinds of wines from acquired values of the pH, the alcohol concentration, and the free sulfite concentration;
  enclosing the multiple kinds of wines into aluminum cans of an identical type, respectively, thereby obtaining multiple kinds of canned wines;
  putting the multiple kinds of canned wines in storage and evaluating quality of the canned wines after the storage; and
  determining an upper limit value of the molecular $SO_2$ concentration based on an evaluation result obtained from the evaluating.

<A2> The method according to <A1>, further including:
  acquiring a chloride ion concentration for the multiple kinds of wines; and
  determining an upper limit value of the chloride ion concentration within a range not exceeding 350 mg/L based on the evaluation result obtained from the evaluating.

<A3> The method according to <A1> or <A2>, wherein
  the aluminum can includes an aluminum sheet, a resin film provided on a surface of the aluminum sheet which faces an internal space (an interior) of the aluminum can, and an adhesive layer interposed between the aluminum sheet and the resin film and bonding the aluminum sheet and the resin film together,
  the resin film includes a first resin layer as a topmost layer and a second resin layer containing a dimer acid-copolymerized polyester resin, and
  at least one of the resin layers constituting the resin film, and/or the adhesive layer contains calcium carbonate.

<A4> The method according to <A3>, wherein
the resin film has a two-layered structure constituted by the first resin layer and the second resin layer.
<A5> The method according to <A3> or <A4>, wherein
the first resin layer contains an isophthalic acid-copolymerized polyester resin.
<A6> The method according to any one of <A3> to <A5>, wherein
the adhesive layer contains a thermosetting epoxy resin.
<A7> The method according to <A3>, wherein
the resin film further includes a third resin layer as an outermost layer facing the adhesive layer, and has a three-layered structure constituted by the first resin layer, the second resin layer, and the third resin layer.
<A8> The method according to <A7>, wherein
the first resin layer contains an isophthalic acid-copolymerized polyester resin.
<A9> The method according to <A7> or <A8>, wherein
the adhesive layer contains a thermosetting epoxy resin.
<A10> The method according to any one of <A7> to <A9>, wherein
the third resin layer contains an isophthalic acid-copolymerized polyester resin.
<A11> The method according to any one of <A3> to <A10>, wherein
the adhesive layer contains calcium carbonate.

6-2. Method for Checking Feasibility of Filling Aluminum can with Wine

<B1> A method for checking feasibility of filling an aluminum can with a wine, the method including:
acquiring a pH, an alcohol concentration, and a free sulfite concentration for a subject wine intended to be enclosed in an aluminum can used in the method according to <A1>;
calculating a molecular $SO_2$ concentration of the subject wine from acquired values of the pH, the alcohol concentration, and the free sulfite concentration; and
excluding the subject wine from wines that are feasible for filling the aluminum can used in the method according to <A1> if the calculated molecular $SO_2$ concentration exceeds the upper limit value of the molecular $SO_2$ concentration determined by the method according to <A1>.
<B2> The method according to <B1>, further including:
acquiring a chloride ion concentration for the subject wine; and
excluding the subject wine from wines that are feasible for filling the aluminum can used in the method according to <A1> if the calculated molecular $SO_2$ concentration exceeds the upper limit value of the molecular $SO_2$ concentration determined by the method according to <A1> or if the acquired chloride ion concentration exceeds the upper limit value of the chloride ion concentration determined by the method according to <A2>.
<B3> The method according to <B1> or <B2>, wherein
the aluminum can includes an aluminum sheet, a resin film provided on a surface of the aluminum sheet which faces an internal space (an interior) of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.
<B4> The method according to <B3>, wherein
the resin film has a two-layered structure constituted by the first resin layer and the second resin layer.
<B5> The method according to <B3> or <B4>, wherein
the first resin layer contains an isophthalic acid-copolymerized polyester resin.
<B6> The method according to any one of <B3> to <B5>, wherein
the adhesive layer contains a thermosetting epoxy resin.
<B7> The method according to <B3>, wherein
the resin film further includes a third resin layer as an outermost layer facing the adhesive layer, and has a three-layered structure constituted by the first resin layer, the second resin layer, and the third resin layer.
<B8> The method according to <B7>, wherein
the first resin layer contains an isophthalic acid-copolymerized polyester resin.
<B9> The method according to <B7> or <B8>, wherein
the adhesive layer contains a thermosetting epoxy resin.
<B10> The method according to any one of <B7> to <B9>, wherein
the third resin layer contains an isophthalic acid-copolymerized polyester resin.
<B11> The method according to any one of <B3> to <B10>, wherein
the adhesive layer contains calcium carbonate.

6-3. Method for Producing Aluminum-Canned Wine

<C1> A method for producing an aluminum-canned wine, the method including:
enclosing a subject wine determined to have a filling feasibility by the method according to any one of <B1> to <B11> into an aluminum can of an identical type to the aluminum can used in the method according to <A1>.
<C2> The method according to <C1>, wherein
the aluminum can includes an aluminum sheet, a resin film provided on a surface of the aluminum sheet which faces an internal space (an interior) of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.
<C3> The method according to <C2>, wherein
the resin film has a two-layered structure constituted by the first resin layer and the second resin layer.
<C4> The method according to <C2> or <C3>, wherein
the first resin layer contains an isophthalic acid-copolymerized polyester resin.
<C5> The method according to any one of <C2> to <C4>, wherein
the adhesive layer contains a thermosetting epoxy resin.
<C6> The method according to <C2>, wherein
the resin film further includes a third resin layer as an outermost layer facing the adhesive layer, and has a three-layered structure constituted by the first resin layer, the second resin layer, and the third resin layer.
<C7> The method according to <C6>, wherein
the first resin layer contains an isophthalic acid-copolymerized polyester resin.
<C8> The method according to <C6> or <C7>, wherein
the adhesive layer contains a thermosetting epoxy resin.

<C9> The method according to any one of <C6> to <C8>, wherein
the third resin layer contains an isophthalic acid-copolymerized polyester resin.

<C10> The method according to any one of <C2> to <C9>, wherein
the adhesive layer contains calcium carbonate.

EXAMPLES

Example 1

In Example 1, the method according to the first aspect was carried out.

<Acquisition of pH, Alcohol Concentration, Free Sulfite Concentration, and Chloride Ion Concentration>

A pH, an alcohol concentration, a free sulfite concentration, and a chloride ion concentration were acquired for 38 kinds of wines. The pH was measured at 20° C. using a pH meter. The alcohol concentration was measured by high performance liquid chromatography. The free sulfite concentration was measured by an aeration distillation and titration method (Rankine's method). The chloride ion concentration was measured by a potentiometric titration method.

<Calculation of Molecular $SO_2$ Concentration>

From the acquired values of the pH, the alcohol concentration, and the free sulfite concentration, the molecular $SO_2$ concentration of each of the 38 kinds of wines was calculated according to the above described formula for calculating molecular $SO_2$ concentrations.

<Enclosure into Aluminum Cans>

The wines were each put in an aluminum can body to fill the same, and a separately provided cap was screwed and secured to each aluminum can body, thereby producing canned wines.

The aluminum cans used had a structure of the bottle can as shown in FIG. 1, and had a resin coating having a layer structure as shown in FIG. 3 on their inner surfaces and a resin coating on their outer surfaces. More specifically, each aluminum can body had, from the outer surface side thereof, an outer-surface-side resin film, an aluminum sheet 10, an adhesive layer 11, and a three-layered inner-surface-side resin film 12.

The three-layered inner-surface-side resin film 12 was constituted by an outer layer made of a 10 mol % isophthalic acid-copolymerized PET resin, an intermediate layer made of a 21 mol % dimer acid-copolymerized PET resin, and an inner layer made of a 10 mol % isophthalic acid-copolymerized PET resin. The inner-surface-side resin film 12 had a thickness of 25 µm. The outer layer, the intermediate layer, and the inner layer had a thickness ratio of 1:1:0.5. The adhesive layer 11 was made of a thermosetting epoxy resin and contained calcium carbonate particles. The adhesive layer 11 had a thickness of 3 µm.

The outer-surface-side resin film was made of a blended resin containing polybutylene terephthalate and isophthalic acid-copolymerized polyethylene terephthalate (PBT/copolymerized PET). The outer-surface-side resin film had a thickness of 18 µm.

The materials of the aluminum cans were prepared in the following manner. The inner-surface-side resin film was prepared by a known co-extrusion film forming method, and an adhesive resin was applied to the inner-surface-side resin film. Meanwhile, the outer-surface-side resin film was prepared by a known film forming method. These two films were then bonded to the aluminum sheet by thermocompression bonding.

<Storage and Quality Evaluation of Canned Wines>

The canned wines were stored, and subjected to quality evaluation after the storage. The storage was carried out for a period of 24 months at temperatures of 5° C., 20° C., and 38° C. The quality evaluation was performed by visual observation of corrosion states and sensory evaluation.

If, under all the storage conditions, no corrosion was observed and no deterioration of wine flavor occurred, the wine was rated as a wine feasible for filling the tested aluminum can. If corrosion was observed, or if the wine flavor deteriorated, the wine was rated as a wine not feasible for filling the tested aluminum can.

<Determination of Upper Limit Value of Molecular $SO_2$ Concentration and Upper Limit Value of Chloride Ion Concentration>

Data of each wine was plotted with reference to a horizontal axis representing the molecular $SO_2$ concentration (mg/L) and a vertical axis representing the chloride ion concentration (mg/L). Plotting of wines with good evaluation results (i.e., wines evaluated as being applicable to the tested aluminum cans) used a mark "o", and plotting of wines with poor evaluation results (i.e., wines evaluated as being inapplicable to the tested aluminum cans) used a mark "x".

FIG. 4 shows the evaluation results. It has been demonstrated by the evaluation results that the concentration of molecular $SO_2$ in wines had a close correlation with corrosion of aluminum cans and degradation of wine flavor. The concentration of chloride ions in the wines did not exceed the upper limit value of the content allowed for food products (i.e., 350 mg/L).

Based on the evaluation results, the upper limit value of the molecular $SO_2$ concentration was successfully determined to be 4.3 mg/L. In more concrete terms, the upper limit value of the molecular $SO_2$ concentration was set to 90% of the value of the highest molecular $SO_2$ concentration among the wines with good evaluation results. Based on the evaluation results, the upper limit value of the chloride ion concentration was also successfully determined to be 350 mg/L.

As described above, carrying out the method according to the first aspect enables the determination of a reference value of a wine feasible for filling a specific aluminum can in advance. Based on this reference value, whether or not filling the aluminum can with a subject wine is feasible (that is, whether or not corrosion resistance is guaranteed if the subject wine is stored in the aluminum can) can be checked. This eliminates the necessity of conducting conventionally required storage tests, and accordingly, the time required for the commercialization of aluminum-canned wines can be reduced.

Example 2

In Example 2, storage tests were conducted where the three kinds of wines shown in Table 1 below were enclosed in the aluminum cans as used in Example 1 (which will be called "aluminum cans A") and also in another type of aluminum cans (which will be called "aluminum cans B"). The storage tests were carried out as described in the section <Storage and Quality Evaluation of Canned Wines> Set Forth in Relation to Example 1.

The aluminum cans B had a structure of a bottle can, and had a resin coating having a layer structure as shown in FIG.

2 on their inner surfaces and a resin coating on their outer surfaces. More specifically, the body of each aluminum can B had, from the outer surface side thereof, an outer-surface-side resin film, an aluminum sheet 10, an adhesive layer 11, and a two-layered inner-surface-side resin film 12.

The two-layered inner-surface-side resin film 12 was constituted by an outer layer made of a blended resin containing polybutylene terephthalate and polyethylene terephthalate (PBT/PET) and an inner layer made of a 10 mol % isophthalic acid-copolymerized polyester resin. The inner-surface-side resin film 12 had a thickness of 20 μm. The outer layer and the inner layer had a thickness ratio of 1:1. The adhesive layer 11 was made of a thermosetting epoxy resin and contained calcium carbonate particles. The adhesive layer 11 had a thickness of 3 μm.

The outer-surface-side resin film was made of a blended resin containing polybutylene terephthalate and polyethylene terephthalate (PBT/PET). The outer-surface-side resin film had a thickness of 18 μm.

The table below shows the evaluation results.

TABLE 1

| Can | Wine | pH | Alcohol (%) | Free sulfite (mg/L) | Chloride ion (mg/L) | Result of corrosion resistance evaluation |
|---|---|---|---|---|---|---|
| Aluminum can A | Wine A | 2.9 | 8 | 24 | 170 | Not corroded |
| Aluminum can A | Wine B | 3.5 | 12 | 26 | 40 | Not corroded |
| Aluminum can A | Wine C | 3.0 | 12 | 30 | 50 | Not corroded |
| Aluminum can B | Wine A | 2.9 | 8 | 24 | 170 | Corroded |
| Aluminum can B | Wine B | 3.5 | 12 | 26 | 40 | Not corroded |
| Aluminum can B | Wine C | 3.0 | 12 | 30 | 50 | Corroded |

The wine A that was enclosed in the aluminum can A and subjected to the storage test did not cause corrosion, while the wine A that was enclosed in the aluminum can B and subjected to the storage test caused corrosion. Similarly, the wine C that was enclosed in the aluminum can A and subjected to the storage test did not cause corrosion, while the wine C that was enclosed in the aluminum can B and subjected to the storage test caused corrosion. It can be seen from these results that, in the context of determining a reference value of a wine (e.g., an upper limit value of the molecular $SO_2$ concentration) in line with the method according to the present invention, the reference value needs to be determined for each type of aluminum can.

Also, by comparison, the aluminum can A had higher corrosion resistance than the aluminum can B. In the aluminum can A, the inner-surface-side resin film includes a resin layer as a topmost layer and a resin layer containing a dimer acid-copolymerized polyester resin, and the adhesive layer for bonding the resin film contains calcium carbonate. It can be seen from the results that the aluminum can having such a resin coating on its inner surface is excellent as an aluminum can to be filled with wine.

REFERENCE SIGNS LIST

1 . . . Aluminum can to be filled with wine
2 . . . Container body
2a . . . Spout neck portion
2b . . . Shoulder portion
2c . . . Trunk portion
3 . . . Bottom lid
10 . . . Aluminum sheet
11 . . . Adhesive layer
12 . . . Resin film
12a . . . First resin layer
12b . . . Second resin layer
12c . . . Third resin layer
14 . . . Calcium carbonate

What is claimed is:

1. A method for determining a reference value of a wine for feasibility of filling an aluminum can, the method comprising:
   acquiring a pH, an alcohol concentration, and a free sulfite concentration for multiple kinds of wines;
   calculating a molecular $SO_2$ concentration of each of the multiple kinds of wines from acquired values of the pH, the alcohol concentration, and the free sulfite concentration;
   enclosing the multiple kinds of wines into aluminum cans of an identical type, respectively, thereby obtaining multiple kinds of canned wines;
   putting the multiple kinds of canned wines in storage and evaluating quality of the canned wines after the storage; and
   determining an upper limit value of the molecular $SO_2$ concentration based on an evaluation result obtained from the evaluating.

2. A method for checking feasibility of filling an aluminum can with a wine, the method comprising:
   determining the upper limit value of the molecular $SO_2$ concentration in accordance with the method according to claim 1;
   acquiring a pH, an alcohol concentration, and a free sulfite concentration for a subject wine intended to be enclosed in an aluminum can used in the method according to claim 1;
   calculating a molecular $SO_2$ concentration of the subject wine from acquired values of the pH, the alcohol concentration, and the free sulfite concentration; and
   excluding the subject wine from wines that are feasible for filling the aluminum can used in the method according to claim 1 if the calculated molecular $SO_2$ concentration exceeds the upper limit value of the molecular $SO_2$ concentration determined above.

3. The method according to claim 2, further comprising:
   acquiring a chloride ion concentration for the multiple kinds of wines;
   determining an upper limit value of the chloride ion concentration within a range not exceeding 350 mg/L based on the evaluation result obtained from the evaluating;
   acquiring a chloride ion concentration for the subject wine; and
   excluding the subject wine from wines that are feasible for filling the aluminum can used in the method according to claim 2 if the calculated molecular $SO_2$ concentration exceeds the upper limit value of the molecular $SO_2$ concentration determined by the method according to claim 2 or if the acquired chloride ion concentration exceeds the upper limit value of the chloride ion concentration determined above.

4. A method for producing an aluminum-canned wine, the method comprising:
   checking feasibility of filling an aluminum can with a wine in accordance with the method according to claim 3; and enclosing a subject wine determined to have a filling feasibility by the method according to claim 3 into an aluminum can of an identical type to the aluminum can used in the method according to claim 3.

5. The method according to claim 4, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

6. The method according to claim 3, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

7. A method for producing an aluminum-canned wine, the method comprising:
checking feasibility of filling an aluminum can with a wine in accordance with the method according to claim 2; and
enclosing a subject wine determined to have a filling feasibility by the method according to claim 2 into an aluminum can of an identical type to the aluminum can used in the method according to claim 2.

8. The method according to claim 7, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

9. The method according to claim 2, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

10. The method according to claim 1, further comprising:
acquiring a chloride ion concentration for the multiple kinds of wines; and
determining an upper limit value of the chloride ion concentration within a range not exceeding 350 mg/L based on the evaluation result obtained from the evaluating.

11. The method according to claim 10, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

12. The method according to claim 1, wherein
the aluminum can includes an aluminum sheet, a resin film provided on a surface of the aluminum sheet which faces an internal space of the aluminum can, and an adhesive layer interposed between the aluminum sheet and the resin film and bonding the aluminum sheet and the resin film together,
the resin film includes a first resin layer as a topmost layer and a second resin layer containing a dimer acid-copolymerized polyester resin, and
at least one of the resin layers constituting the resin film, and/or the adhesive layer contains calcium carbonate.

* * * * *